US010772813B2

(12) United States Patent
Acs

(10) Patent No.: US 10,772,813 B2
(45) Date of Patent: Sep. 15, 2020

(54) COMPOSITIONS AND METHODS OF ADMINISTERING A COLCHICINE BASED TOPICAL COMPOSITION FOR THE PREVENTION OF RADIATION FIBROSIS

(71) Applicant: Colradel, LLC, Gainesville, FL (US)

(72) Inventor: Peter I. Acs, Gainesville, FL (US)

(73) Assignee: COLRADEL, LLC, Gainesville, FL (US)

( * ) Notice: Subject to any disclaimer, the term of this patent is extended or adjusted under 35 U.S.C. 154(b) by 353 days.

(21) Appl. No.: 15/612,261

(22) Filed: Jun. 2, 2017

(65) Prior Publication Data

US 2017/0348211 A1 Dec. 7, 2017

Related U.S. Application Data

(60) Provisional application No. 62/345,446, filed on Jun. 3, 2016.

(51) Int. Cl.
| | | |
|---|---|---|
| A61K 8/42 | (2006.01) | |
| A61K 8/49 | (2006.01) | |
| A61K 8/67 | (2006.01) | |
| A61Q 17/04 | (2006.01) | |
| A61Q 19/00 | (2006.01) | |
| A61P 17/16 | (2006.01) | |
| A61P 17/02 | (2006.01) | |

(52) U.S. Cl.
CPC ............... *A61K 8/42* (2013.01); *A61K 8/4953* (2013.01); *A61K 8/678* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,565,462 | A | 10/1996 | Eitan et al. |
| 6,291,516 | B1 | 9/2001 | Dudek et al. |
| 6,294,350 | B1 | 9/2001 | Peterson |
| 7,319,109 | B2 | 1/2008 | Boggs et al. |
| 7,705,028 | B2 | 4/2010 | Caldwell et al. |
| 7,863,253 | B2 | 1/2011 | Jagtap et al. |
| 7,915,225 | B2 | 3/2011 | Finck |
| 7,998,974 | B2 | 8/2011 | Milburn et al. |
| 8,058,259 | B2 | 11/2011 | Thompson et al. |
| 9,029,385 | B2 | 5/2015 | Raghu et al. |
| 9,084,746 | B2 | 7/2015 | Wang et al. |
| 9,585,962 | B1 * | 3/2017 | Moy ...................... A61K 47/40 |
| 2011/0183948 | A1 | 7/2011 | Levine et al. |
| 2014/0343057 | A1 | 11/2014 | Palombella et al. |
| 2015/0335674 | A1 | 11/2015 | Kottmann et al. |

FOREIGN PATENT DOCUMENTS

| | | | | |
|---|---|---|---|---|
| WO | WO-9745098 A2 | * | 12/1997 | ............. A61K 8/678 |
| WO | WO-2005070433 A1 | * | 8/2005 | ........... A61K 31/522 |

OTHER PUBLICATIONS

Grimaitre, M., et al. "Topical colchicine therapy for actinic keratoses." Dermatology 200.4 (2000): 346-348.*
Martin, Michèle, Jean-Louis Lefaix, and Sylvie Delanian. "TGF-β1 and radiation fibrosis: a master switch and a specific therapeutic target?." International Journal of Radiation Oncology* Biology* Physics 47.2 (2000): 277-290.*
Lampen, P., et al. "Penetration studies of vitamin E acetate applied from cosmetic formulations to the stratum cornum of an in vitro model using quantification by tape stripping, UV spectroscopy, and HPLC." J. Cosmet. Sci 54 (2003): 119-131.*
Kaidbey, Kays H., John W. Petrozzi, and Albert M. Kligman. "Topical colchicine therapy for recalcitrant psoriasis." Archives of dermatology 111.1 (1975): 33-36.*
Guéniche, Audrey, et al. "Bifidobacterium longum lysate, a new ingredient for reactive skin." Experimental dermatology 19.8 (2010): e1-e8.*
Kulcu Cakmak, Seray, et al. "Pentoxifylline use in dermatology." Inflammation & Allergy—Drug Targets (Formerly Current Drug Targets—Inflammation & Allergy) 11.6 (2012): 422-432.*
Diegelmann, R. F. and Peterkofsky, B. Inhibition of Collagen Secretion from Bone and Cultured Fibroblasts by Microtubular Disruptive Drugs. Proc Natl Acad Sci U S A. Apr. 1972; 69(4):892-896, 5 pages.
Trnavská, Z., Mikullková, D., Trnavský, K. discuss The effects of colchicine and its derivates on the collagen biosynthesis in vitro. Immunosuppression and Inflammation. Agents and Actions. Dec. 1977; 7(5):563-567, 5 pages.
Lemor, M., de Bustros, S., Glaser, B. M. Low-Dose Colchicine Inhibits Astrocyte, Fibroblast, and Retinal Pigment Epithelial Cell Migration and Proliferation. Archives of Ophthalmology. Sep. 1986; 104(8):1223-5, 3 pages.
Mansour, M. M., Dunn, M. A., Salah, L. A. Effect of colchicine on collagen synthesis by liver fibroblasts in murine schistosomiasis. Clinica Chimica Acta. Sep. 1988; 177(1):11-20, 10 pages.
Kershenobich, D., Vargas, F., Garcia-Tsao, G., Perez Tamayo, R., Gent, M., Rojkind, M. Colchicine in the treatment of cirrhosis of the liver. N Engl J Med Jun. 1988; 318:1709-1713, 5 pages.

(Continued)

*Primary Examiner* — Bethany P Barham
*Assistant Examiner* — Peter Anthopolos
(74) *Attorney, Agent, or Firm* — Brian S. Steinberger; Hilary F. Steinberger; Law Offices of Brian S. Steinberger, P.A.

(57) ABSTRACT

A colchicine-containing composition comprising colchicine as the active ingredient or colchicine in combination with pentoxifylline and tocopherol (Vitamin E) which are formulated for topical use in the prevention and treatment of radiation-induced fibrosis. And methods of making and administering the colchicine-containing compositions. The compositions can be used as topical applications for the prevention and treatment of radiation-induced fibrosis, commonly known as scarring, that can be debilitating, and can occur as a late and permanent complication of radiation therapy.

6 Claims, No Drawings

(56) References Cited

OTHER PUBLICATIONS

Alberts DS, Goldman R, Xu MJ, et al. Disposition and metabolism of topically administered alpha-tocopherol acetate: a common ingredient of commercially available sunscreens and cosmetics. Nutr Cancer. 1996; 26(2):193-201, 9 pages.
Traber MG, Rallis M, Podda M, Weber C, Maibach HI, Packer L. Penetration and distribution of alpha-tocopherol, alpha- or gamma-tocotrienols applied individually onto murine skin. Lipids. 1998; 33(1):87-91, 5 pages.
Delanian, S. Striking regression of radiation-induced fibrosis by a combination of pentoxifylline and tocopherol. Br J Radiol. Aug. 1998; 71(848):892-4, 3 pages.
Okunieff, P., Augustine, E., Hicks, J. E., Cornelison, T., Altemus, R., Naydich, B. G. Pentoxifylline in the treatment of radiation-induced fibrosis. Journal of Clinical Oncology. Jul. 2004; 22(11):2207-13, 7 pages.
Thiele JJ, Ekanayake-Mudiyanselage S. Vitamin E in human skin: organ-specific physiology and considerations for its use in dermatology. Mol Aspects Med. 2007; 28(5-6):646-667, 22 pages.
Burke, Karen E., Chapter 4: Photoprotection of the Skin with Vitamins C and E: Antioxidants and Synergies. Nutrition and Skin: Lessons for Anti-Aging, Beauty and Healthy Skin, Springer Science, 2011: 43-58, 16 pages.
Nada A, Krishnaiah YS, Zaghloul AA, Khattab I. In vitro and in vivo Permeation of Vitamin E and Vitamin E Acetate from Cosmetic Formulations. Med Princ Pract. 2011; 20(6):509-513, 6 pages.
Lawenda, B. D. Reduce skin fibrosis & possibly breast implant contracture after radiation therapy: vitamin E & pentoxifylline. Integrative Oncology Essential. Aug. 2011, 3 pages.
Loiselle, C. Vitamin E, Pentoxifylline, and Radiation Fibrosis. Global Resource for Advancing Cancer Education. Nov. 2011, 2 pages.
Maduri, S., Atla, V. R. Formulation of colchicine ointment for the treatment of acute gout. Singapore Med J. Nov. 2012; 53(11):750-4, 5 pages.

\* cited by examiner

COMPOSITIONS AND METHODS OF ADMINISTERING A COLCHICINE BASED TOPICAL COMPOSITION FOR THE PREVENTION OF RADIATION FIBROSIS

CROSS REFERENCE TO RELATED APPLICATION

This application claims the benefit of priority to U.S. Provisional Application Ser. No. 62/345,446 filed Jun. 3, 2016, which is incorporated by reference in its' entirety.

FIELD OF INVENTION

This invention relates to colchicine, and more particularly to compositions comprising colchicine as the bioactive ingredient or colchicine in combination with pentoxifylline and tocopherol (Vitamin E) formulated for topical use in the prevention and treatment of radiation-induced fibrosis, commonly known as scarring, that can be debilitating, and can occur as a late and permanent complication of radiation therapy, and to methods of making and methods of administering the composition.

BACKGROUND AND PRIOR ART

Radiation-induced fibrosis or scarring is a side-effect of radiation therapy which is characterized by scarring and hardening of tissue inside the body or on the skin. This side-effect can appear in a number of different locations, and may cause additional complications for the patient, depending on where it manifests.

Radiation fibrosis is a significant issue in multiple diseases, most importantly in scarring after radiation treatment for head and neck cancer and breast cancer. Radiation fibrosis refers to a transformation from soft, supple, and pliable soft tissue to one that is stiffer, less flexible, and less able to normally withstand and repair after minor injuries. On the cellular level, radiation induced fibrosis has been linked to abnormal fibroblast activity.

Fibroblasts normally help tissues repair after injury, but in situations of radiation induced fibrosis, these cells overreact, and can produce excessive extracellular matrix or collagen around healthy cells. During radiation the initial inflammation, triggered by therapeutic ionizing radiation, spirals out of control and the inflammatory response turns chronic, with significant resultant scarring.

Radiation changes during treatment may be substantial but the late changes are more debilitating ultimately causing a major decline in quality of life. In head and neck cancer these radiation changes lead to chronic scarring resulting in problems with speech, breathing and swallowing that frequently bring about severe weight loss and sleep apnea. Fibrosis also restricts the range of motion of the neck and certainly leaves chronic cosmetic after effects and injury.

While radiation fibrosis cannot be completely avoided, there are treatments which can be used to manage it, and there are also some steps which can be taken to reduce the risk that it will develop.

It is believed that radiation fibrosis is probably closely linked with lymphedema, which can cause permanent damage to body tissues. Consistent inflammation and irritation often leads to scarring and hardening over time, which in turn makes it more difficult for lymph to circulate, and can cause the lymphedema and fibrosis to spread. Radiation fibrosis can appear weeks or months after radiation therapy, and may grow substantially worse over time.

On skin areas, fibrosis can be a cosmetic issue because it makes the skin look unsightly. In addition, it may restrict freedom of movement because the scarred skin is usually stiff and tough. Radiation fibrosis on the neck, for example, might make it hard for a patient to turn her or his head, because the scarring pulls at the neck. Fibrosis can also occur in internal organs such as the lungs, in which case it may cause secondary complications such as difficulty breathing and susceptibility to infection in the future as a result of the compromised tissue.

Some medications may be helpful for people with radiation fibrosis. In the case of scarring on the skin, gentle stretching, massage, and other exercises can promote freedom of movement or help patients retain their current freedom of movement. Radiation-induced fibrosis inside the body is treated on a case by case basis, depending on the nature of the damage, and medical imaging studies of the involved area may be required in order to develop a treatment plan.

International scientific and medical journals have focused on various formulations for treating fibrosis; representative publications are listed below in chronological order.

Diegelmann, R. F. and Peterkofsky, B. Inhibition of Collagen Secretion from Bone and Cultured Fibroblasts by Microtubular Disruptive Drugs. *Proc Natl Acad Sci USA*. July 1972; 69 (4):892-896 teaches that colchicine blocks the production and secretion of collagen.

Trnayská, Z., Mikulíková, D., Trnayský, K. discuss "The effects of colchicine and its derivates on the collagen biosynthesis in vitro. *Immunosuppression and Inflammation. Agents and Actions*. December 1977; 7 (5):563-567.

Lemor, M., de Bustros, S., Glaser, B. M. Low-Dose Colchicine Inhibits Astrocyte, Fibroblast, and Retinal Pigment Epithelial Cell Migration and Proliferation. *Archives of Ophthalmology*. September 1986; 104 (8):1223-5.

Mansour, M. M., Dunn, M. A., Salah, L. A. Effect of colchicine on collagen synthesis by liver fibroblasts in murine schistosomiasis. *Clinica Chimica Acta*. September 1988; 177 (1):11-20.

Kershenobich, D., Vargas, F., Garcia-Tsao, G., Perez Tamayo, R., Gent, M., Rojkind, M. Colchicine in the treatment of cirrhosis of the liver. *N Engl J Med* June 1988; 318:1709-1713 wherein colchicine is used in the treatment of liver cirrhosis, a disease caused by scarring. Despite the chronic use of enterally administered colchicine, there were very few side effects.

Alberts D S, Goldman R, Xu M J, et al. Disposition and metabolism of topically administered alpha-tocopherol acetate: a common ingredient of commercially available sunscreens and cosmetics. *Nutr Cancer*. 1996; 26 (2):193-201, Vitamin E (tocopherol) is a very common ingredient in sunscreens and cosmetic formulations.

Traber M G, Rallis M, Podda M, Weber C, Maibach H I, Packer L. Penetration and distribution of alpha-tocopherol, alpha- or gamma-tocotrienols applied individually onto murine skin. *Lipids*. 1998; 33 (1):87-91, teach Vitamin E (tocopherol) levels in the dermis increase greatly after topical application.

Delanian, S. Striking regression of radiation-induced fibrosis by a combination of pentoxifylline and tocopherol. *Br J Radiol*. August 1998; 71 (848):892-4, teach that pentoxifylline, along with tocopherol (Vitamin E) has been used successfully to treat radiation fibrosis. The treatments were not preventive treatments and the formulation was administered orally.

Okunieff, P., Augustine, E., Hicks, J. E., Cornelison, T., Altemus, R., Naydich, B. G. Pentoxifylline in the treatment of radiation-induced fibrosis. *Journal of Clinical Oncology.* July 2004; 22 (11):2207-13, teach that the single agent, oral pentoxifylline, resulted in significant improvement in late radiation-induced fibrosis. Pentoxifylline is used in topical formulations by Stroud Compounding and Wellness company. Thiele J J, Ekanayake-Mudiyanselage S. Vitamin E in human skin: organ-specific physiology and considerations for its use in dermatology. *Mol Aspects Med.* 2007; 28 (5-6):646-667, provides evidence that solutions with Vitamin E (tocopherol) concentrations as low as 0.1% can increase Vitamin E levels in the skin.

Burke, Karen E., Chapter 4: Photoprotection of the Skin with Vitamins C and E: Antioxidants and Synergies. *Nutrition and Skin: Lessons for Anti-Aging, Beauty and Healthy Skin*, Springer Science, 2011: 43-58, teaches that vitamin E absorbs well through the skin and a much higher (11 times more) concentration is achievable by topical administration than with high doses orally. Vitamin E is more protective topically than with oral administration. A composition is provided that maintains stability and delivers active antioxidant to the deep layers of the skin in the d-alpha-tocopherol form, optimally at a concentration of 2-5%.

Nada A, Krishnaiah Y S, Zaghloul A A, Khattab I. In vitro and in vivo Permeation of Vitamin E and Vitamin E Acetate from Cosmetic Formulations. *Med Princ Pract.* 2011; 20 (6):509-513, teaches and provides further evidence that Vitamin E (tocopherol) is very well absorbed through skin. Vitamin E levels in the dermis increase greatly after topical application.

Lawenda, B. D. Reduce skin fibrosis & possibly breast implant contracture after radiation therapy: vitamin E & pentoxifylline. *Integrative Oncology Essential.* August 2011, teaches that pentoxifylline is used in the management of peripheral artery disease, leg ulcers, strokes, high-altitude sickness, eye and ear disorders, and sickle cell disease, and diabetic neuropathy. Pentoxifylline, along with tocopherol (vitamin E) has been used to treat radiation fibrosis.

Loiselle, C. Vitamin E, Pentoxifylline, and Radiation Fibrosis. *Global Resource for Advancing Cancer Education.* November 2011, teaches that during radiation, the inflammation triggered by therapeutic ionizing radiation, spirals out of control and the inflammatory response turns chronic, with significant resultant scarring.

Maduri, S., Atla, V. R. Formulation of colchicine ointment for the treatment of acute gout. *Singapore Med J.* November 2012; 53 (11):750-4, teaches that colchicine may have adverse effects associated with its administration through the enteral and parenteral routes, but the preparation of dosage forms of colchicine were administered by alternative routes. Based on this study, among the formulations and dosage forms of colchicine, its ointment was a good option available due to its ability to deliver the drug transdermally as well as its ease of preparation and evaluation. Maduri et al. prepared and tested 0.2% and 0.5% colchicine ointments for effectiveness in delivering colchicine transdermally. Colchicine was found to be well-absorbed transdermally for treatment of gout, with no side effects associated with its 0.2% formulation (0.2 gram in 100 ml). 0.2% colchicine achieved the same concentration in the skin as 0.5%. There was no recognition of the use of the colchicine ointment other than for treatment of gout.

Various patents have attempted to solve the problem of radiation-induced fibrosis.

U.S. Pat. No. 5,565,462 to Eitan et al. describes a Composition for Topical Treatment of Psoriasis and Atopic Dermatitis Comprising a Xanthine Derivative. A compound selected from the group of pentoxifylline, propentofylline and torbafylline for improving psoriatic lesions is used topically. The composition uses vitamin A, vitamin D and delta tocopherol for treatment of psoriasis, but does not suggest using the composition of the present invention for treatment and prevention of radiation-induced fibrosis.

U.S. Pat. No. 6,291,516 to Dudek et al. describes Regulators of the Hedgehog Pathway, Compositions and Uses Related Thereto. Treating actinic dermatitis is disclosed. The condition is due to exposure to actinic radiation such as from the sun, ultraviolet waves or x- or gamma radiation and maybe topical formulations when treating epidermal tissue. The composition may include a cAMP inhibitor which may be pentoxifylline and alpha-tocopherol; there is no suggestion or teaching to use the composition of the present invention.

U.S. Pat. No. 6,294,350 to Peterson describes Methods for Treating Fibroproliferative Diseases. Treating radiation induced fibrosis with a cJun antisense compound is disclosed. The composition may comprise pentoxifylline and tocopherol and colchicine; and mixtures thereof. The active components may be delivered transdermally, topically, or by inhalation. A specific formulation for prevention of radiation-induced fibrosis is not provided.

U.S. Pat. No. 7,319,109 to Boggs et al. describes Farnesoid X Receptor Agonists. Compositions specifically prepared for fibrosis caused by radiation are disclosed. Pharmaceutical compositions may be adapted for topical administration and may be formulated as ointments, creams, suspensions, lotions, powders, solutions, pastes, gels, sprays, aerosols or oils. The compositions may include vitamin E. Colchicine is mentioned as an anti-inflammatory substance known for use in treating inflammation that can lead to liver fibrosis.

U.S. Pat. No. 7,705,028 to Caldwell et al. describes a Farnesoid X Receptor Agonists. Pharmaceutical formulations for treating radiation induced liver fibrosis are disclosed. The reference teaches colchicine's known use as a liver fibrosis treating agent.

The formulations may be administered for topical administration as by ointments, creams, suspensions, lotions, powders, solutions, pastes, gels, sprays, aerosols or oils. The formulation includes other therapeutic agents which may be vitamin E.

U.S. Pat. No. 7,863,253 to Jagtap et al. describes Purine Derivatives and Methods of Use Thereof. Purine derivatives and compositions for treating radiation induced injury are disclosed. The formulations may take the form of sprays or topically. Table 2 lists colchicine and colchicine derivatives as antimitotic agents.

U.S. Pat. No. 7,915,225 to Finck describes a Soluble Tumor Necrosis Factor Receptor Treatment of Medical Disorders. Using TNFR:Fc or TNFR:Fc combined with a cytokine used for treating radiation-induced pulmonary fibrosis and to inhibit scarring are disclosed. The composition may further include colchicine and pentoxifylline. The treatment may be a topical preparation; such as, lotions, gels, sprays, ointments. A specific formulation for prevention of radiation-induced fibrosis is not provided.

U.S. Pat. No. 7,998,974 to Milburn et al. describes a Fused Heterocyclic Compounds are disclosed and Their Use as sirtuin Modulators. Sirtuin-modulating compounds which are used in therapeutic treatments increase the life-span of a cell. The compounds may be used in cancer treatment. The treating agents may include pentoxifylline and vitamin E. The treating agent may further include colchicine. The formulation can be lotions, creams or gels. A specific formulation for prevention of radiation-induced fibrosis is not provided.

U.S. Pat. No. 8,058,259 to Thompson et al. describes Substituted 4-{3-[6-Amino-9-(3, 4-Dihydroxy-Tetrahydro-Furan-2-yl)-9h-Purin-2-yl]-prop-2-ynyl}-Piperidine-1-Carboxylic Acid Esters as $A_{2A}$ R Agonists. Purine based compounds used in inflammatory response treatments are disclosed which include dermatitis, eczema, sclerosis and other skin diseases. The compositions may include colchicine and may be topical. A specific formulation for prevention of radiation-induced fibrosis is not provided.

U.S. Pat. No. 9,029,385 to Raghu et al. describes Compositions and Methods for Treating Fibroproliferative Disorders. Radiation-induced, genetic/familial fibrosis treatment compositions are disclosed. The pharmaceutical composition can be in the form of a gel including hydrogel, paste, ointment, cream, spray or lotion. The compositions use pentoxifylline. Table 1, VI uses vitamin E. Colchicine is described as a substance that inhibits fibroblast-like cell proliferation.

U.S. Pat. No. 9,084,746 to Wang et al. describes Therapeutic Applications of Smad7. Smad7 compositions are delivered locally or systemically to a site of inflammation and/or tissue damage for prevention of side effects caused by radiation. The compositions may be applied as creams, salves, ointments, patches, liposomes, nanoparticles, microparticles, timed-release formulations and other materials known in the art for delivery to the oral cavity and/or to the skin. Smad7 compositions comprise tocopherol and pentoxifylline. The reference teaches microtubule inhibitors may be used.

Published Patent Application 2011/0183948 to Levine et al. describes a Treatment of Fibrotic Conditions using Hedgehog Inhibitors. Treating a fibrotic condition due to radiation with a hedgehog inhibitor is disclosed. The composition further contains Vitamin E, pentoxifylline, and colchicine in the treatment of liver fibrosis.

Published Patent Application 2014/0343057 to Palombella et al. describes a Treatment of Lupus, Fibrotic Conditions, and Inflammatory Myopathies and Other Disorders using PI3 Kinase Inhibitors. Topical compositions for treating a radiation fibrotic condition are disclosed. In addition to the PI3 Kinase Inhibitor, the compositions may include vitamin E, pentoxifylline, and colchicine.

Published Patent Application 2015/0335674 to Kottmann et al. describes LDH Inhibitors as Treatment for Fibrosis and Fibrotic-Related Disorders. Treating fibrotic conditions of the lung and other internal organs and tissue due to secondary radiation exposure is disclosed. The treating agents are lactic dehydrogenase inhibitors and may include colchicine, pentoxifylline and tocopherol. The treatment may be applied either transdermal patches, atomizers, or with liposomes. The agents may be used as an aerosol.

As shown in the prior art, fibrotic conditions were treated with specially prepared or synthesized organic compounds, such as, xanthine derivatives, hedgehog inhibitors, cJun antisense compounds, Farnesoid X Receptor agonists, purine derivatives, sirtuin-modulating compounds, Smad7 compositions, PI3 Kinase inhibitors and the like. Often these specially prepared organic compounds, referred to as pharmaceutical compositions or drugs are combined with pentoxifylline, tocopherol (Vitamin E), or colchicine. There is no teaching, suggestion or disclosure that colchicine alone or in combination with pentoxifylline and tocopherol (Vitamin E) could be used as a topical transdermal treatment to prevent or relieve the damaging or injurious effect of radiation-induced fibrosis.

SUMMARY OF THE INVENTION

A primary objective of this invention is to provide a composition of matter and methods of administering the colchicine-containing compositions useful in preventing the formation of scars due to radiation exposure.

A secondary objective of this invention is to provide a composition of matter and methods of administering the colchicine-containing compositions useful in treating scars that have been formed during radiation treatment.

A third objective of this invention is to provide a composition of matter comprising colchicine and methods of administering the colchicine-containing compositions to prevent the formation of scars due to radiation exposure.

A fourth objective of this invention is to provide a composition of matter comprising colchicine and methods of administering the colchicine-containing compositions to treat scars that have been formed during radiation treatment.

A fifth objective of this invention is to provide a composition of matter comprising colchicine and pentoxifylline and methods of administering the colchicine-containing compositions to prevent the formation of scars due to radiation exposure.

A sixth objective of this invention is to provide a composition of matter comprising colchicine and pentoxifylline and methods of administering the colchicine-containing compositions to treat scars that have formed during radiation treatment.

A seventh objective of this invention is to provide a composition of matter comprising colchicine, pentoxifylline and tocopherol (Vitamin E) and methods of administering the colchicine-containing compositions to prevent the formation of scars due to radiation exposure.

An eighth objective of this invention is to provide a composition of matter comprising colchicine, pentoxifylline and tocopherol (Vitamin E) and methods of administering the colchicine-containing compositions to treat scars that have formed during radiation treatment.

A ninth objective of this invention is to provide a method of preventing radiation-induced fibrosis in a mammal by topical administration of a colchicine containing composition of matter and methods of administering the colchicine-containing compositions.

A tenth objective of this invention is to provide a method of treating radiation-induced fibrosis in a mammal by topical administration of a colchicine containing composition of matter and methods of administering the colchicine-containing compositions.

A colchicine-containing composition can include a topical composition that includes colchicine as an active ingredient that is adapted to be applied to the skin for preventing formation of scars due to radiation exposure The topical composition can solely include one active ingredient for preventing the formation of scars due to radiation exposure that is the colchicine.

The topical composition can further include pentoxifylline and tocopherol.

The topical composition (per 100 ml) can include approximately 0.1 gram to approximately 1 gram of colchicine, approximately 1 gram to approximately 20 grams of pentoxifylline, and approximately 100 IU to approximately 5000 IU of d-alpha tocopheryl acetate.

The radiation exposure is from radiation therapy in the treatment of at least one of head and neck cancer and breast cancer as well as any other type of cancer where radiation-induced fibrosis can be an issue.

The topical composition can be in the form of at least one of: suspension, emulsion, solution, gel, paste, ointment, cream, lotion, spray or aerosol.

A colchicine-containing composition can include a topical composition that includes colchicine as an active ingredient that is adapted to be applied to the dermal layer of a mammal to treat radiation-induced scars due to radiation exposure.

Solely, the colchicine can be the one active ingredient for treating the formation of scars due to radiation exposure.

The topical composition can further include pentoxifylline and tocopherol.

The topical composition can include (per 100 ml) approximately 0.1 gram to approximately 1 gram of colchicine, approximately 1 gram to approximately 20 grams of pentoxifylline, and approximately 100 IU to approximately 5000 IU of d-alpha tocopheryl acetate.

The radiation exposure can be from radiation therapy in the treatment of at least one of head and neck cancer and breast cancer as well as any other type of cancer where radiation-induced fibrosis may be an issue.

The composition can be in the form of at least one of: suspension, emulsion, solution, gel, paste, ointment, cream, lotion, spray or aerosol.

A method of preventing radiation-induced fibrosis in a mammal can include the steps of providing a topical administration of a colchicine-containing composition and applying an effective amount of the colchicine-containing composition to an area to be subjected to radiation twice daily beginning on day one of the radiation therapy.

The colchicine-containing composition can include (per 100 ml) approximately 0.1 g to approximately 1 g colchicine.

The colchicine-containing composition can include colchicine, pentoxifylline and tocopherol.

The colchicine-containing composition can include (per 100 ml) approximately 0.1 gram to approximately 1 gram of colchicine, approximately 1 gram to approximately 20 grams of pentoxifylline, and approximately 100 IU to approximately 5000 IU of d-alpha tocopheryl acetate.

The radiation-induced fibrosis can be from radiation therapy in the treatment of at least one of head and neck cancer and breast cancer as well as any other type of cancer where radiation-induced fibrosis may be an issue.

The colchicine-containing composition can be in the form of at least one of: a suspension, emulsion, solution, gel, paste, ointment, cream, lotion, spray or aerosol.

The colchicine-containing composition can be in the form of a cream.

A method of treating radiation-induced fibrosis in a mammal can include the steps of providing a topical administration of a colchicine-containing composition and applying a therapeutic amount of the colchicine-containing composition to an area exhibiting symptoms of radiation fibrosis twice daily for approximately six months to approximately twenty-four months.

Further objects and advantages of this invention will be apparent from the following detailed description of preferred embodiments.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments, reference is made to particular features of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

It is remarkable that the topical administration of colchicine-containing compositions, including colchicine with a pharmaceutically acceptable carrier and colchicine combined with pentoxifylline and tocopherol (Vitamin E) can prevent radiation-induced scarring resulting from radiation therapy.

Scarring on the chest wall from radiation also can result in significant problems in range of motion and chest wall infections that could be extremely persistent due to the lack of blood flow secondary to the hardened connective tissue. All of these late radiation-induced scarring problems are basically permanent; the composition of the present invention can be used to alleviate the symptoms. The primary goal of the present invention is to prevent the formation of these scars. Alternatively, if the radiation fibrosis has begun to form, the colchicine-containing compositions of the present invention can lessen the severity of the scarring.

The individual compounds useful in the composition of the present invention are discussed below.

Colchicine is a yellow, poisonous alkaloid $C_{22}H_{25}NO_6$ that inhibits mitosis, is extracted from the corms or seeds of the autumn crocus (*Colchicum autumnale*), and is used especially in the treatment of gout to relieve pain and in the laboratory to arrest cells during cell division (by disrupting the spindle) so their chromosomes can be visualized.

Colchicine works by disrupting the cytoskeletal functions through inhibition of B-tubulin polymerization into microtubules. This prevents activation, degranulation and migration of neutrophils as well as inhibits migration and proliferation of fibroblasts. It also blocks the production and secretion of collagen. These are the contributing factors to radiation-induced local skin and connective tissue changes. In low doses, without any side effects, colchicine inhibited fibroblast migration by 93%. Colchicine has been successfully used in treatment of liver cirrhosis, a disease caused by scarring.

Pentoxifylline (PTX) (3,7-dimethyl-1-5-(5-oxohexyl)-xanthine) is widely used systemically for the treatment of peripheral vascular diseases. PTX is used to improve the symptoms of a certain blood flow problem in the legs/arms known as, intermittent claudication due to occlusive artery disease. Pentoxifylline can decrease the muscle aching/pain/ cramps during exercise, including walking, that occur with intermittent claudication. Pentoxifylline belongs to a class of drugs known as hemorrheologic agents. It works by helping blood flow more easily through narrowed arteries. This increases the amount of oxygen that can be delivered by the blood when the muscles need more, such as during exercise, thereby increasing walking distance and duration.

With regard to the present invention, pentoxifylline may be involved in blocking the molecular signaling pathway that is responsible for the development of fibrosis as a response to inflammation and injury. Additionally, pentoxifylline increases the flexibility and permeability of red blood cells which enables them to more easily bring oxygen to the tissues and carry carbon dioxide away. It is because of this mechanism that pentoxifylline is used in the management of peripheral artery disease, leg ulcers, strokes, high-altitude sickness, eye and ear disorders, sickle cell disease, and diabetic neuropathy.

Tocopherols are a family of Vitamin E compounds. Vitamin E (tocopherol) is a light yellow oil, a fat-soluble vitamin. The tocopherols are found in nature. Alpha-tocopherol is the most common and the most active of the seven currently described forms—alpha, beta, gamma, delta, epsilon, and zeta. Specifically, d-alpha tocopherol is the most potent form, more active than the synthetic dl-alpha tocopherol.

Vitamin E was discovered in 1922 with experiments on rats. When fed a purified diet devoid of vitamin E, the rats became infertile. Wheat germ oil added to their diet restored their fertility. Later, the oil-based substance was isolated and called the "antisterility" vitamin. Tokos and phero are the Greek words for "offspring" and "to bear," so tocopherol literally means "to bear children." Though there is no clear deficiency disease in humans, vitamin E is well accepted as an essential vitamin.

Alpha-tocopherol is basically stable in heat and in acids; other forms are lost in heat, with storage or freezing, or when oxidized by exposure to the air. Vitamin E is absorbed from the intestines, along with fat and bile salts, first into the lymph and then into the blood, which carries it to the liver to be used or stored. Vitamin E is not stored in the body as effectively as the other fat-soluble vitamins, A, D, and K. Vitamin E is partially absorbed through the skin when used as an ointment or oil application.

Based on the above information and studies, one embodiment of the present invention provides a combination of colchicine and pentoxifylline with the addition of tocopherol as a topical preventive treatment for radiation-induced fibrosis. Colchicine improves very significantly the efficacy of this treatment. By topical administration, the undesired side effects or complications of colchicine are avoided. These three compounds have no interaction making them safe for combined use.

In another embodiment of the invention, colchicine is used topically while pentoxifylline and tocopherol are administered orally.

Example 1

Method for Preventing Radiation Fibrosis

Prior to beginning radiation therapy treatments, the patient in the mammalian species, should apply the colchicine-containing composition of the present invention to the area marked for radiation twice daily starting with day one of radiation treatment.

Continue the twice daily application for a total of six months regardless of when radiation treatment ends. Continue the twice daily applications for an additional six months if symptoms arise.

Example 2

Method for Treating Radiation Fibrosis

If radiation fibrosis symptoms are appearing in a patient of the mammalian species, massage therapy should be started and twice daily application of the colchicine-containing composition of the present invention should be applied to the skin that is exhibiting abnormal fibroblast activity. Apply the colchicine-containing composition for a minimum of 6 months, but typically a year or even up to approximately twenty-four months, as long as improvement in the condition is observed.

Being aware of the risks of radiation fibrosis from the start of radiation therapy is important. Patients should report changes they experience promptly, and they should be monitored throughout treatment for signs of complications and dangerous side effects. The present invention is especially useful for early intervention that can limit side effects, as for example, prior to the first radiation therapy treatment, the topical application of the colchicine-containing product of the present invention can prevent scarring and disfiguring of the area to be subjected to radiation.

TABLE 1 provides a composition of components for using colchicine as the only active ingredient in a topical application (per 100 ml).

TABLE 1

|  | Broad Range | Narrow Range | Preferred |
| --- | --- | --- | --- |
| Active Ingredient |  |  |  |
| Colchicine | approx. 0.1 gram to approx. 1 gram | 0.2 gram to 0.4 gram | approx. 0.2 gram |
| Inactive Ingredient(s) |  |  |  |
| Sodium hyaluronate | 0 to approx. 1 gram | 0.2 gram to 0.4 gram | approx. 0.2 gram |
| Panthenol | 0 to approx. 5 grams | 1 gram to 3 grams | approx. 2 grams |
| Propolis | 0 to approx. 10 grams | 1 gram to 4 grams | approx. 2 grams |
| Sodium metabisulfite | 0 to approx. 1 gram | 0.1 gram to 0.4 gram | approx. 0.2 gram |
| Bifidobacterium longum lysate | 0 to approx. 5 grams | 1 gram to 3 grams | approx. 2 grams |

The composition referenced in Table 1 can be used with colchicine by itself as the active ingredient and with none or one or more of the inactive ingredients. The surface area depends on the size and location of the cancer. Basically, they have to apply to the whole radiation field (marked by tattoo) as well as outside of the marked field if signs of inflammation (redness, swelling, pain) occur.

Colchicine can be made alone or in combination with any or all of the inactive ingredients. We would use these with oral PTX and/or tocopherol or by itself if allergy or contraindications to these ingredients should be present.

TABLE 2 provides a composition of components for using colchicine along with both pentoxifylline and tocopherol as the active ingredients in a topical application (per 100 ml).

TABLE 2

| | Broad Range | Narrow Range | Preferred |
|---|---|---|---|
| Active Ingredients | | | |
| Colchicine | approx. 0.1 gram to approx. 1 gram | 0.2 gram to 0.4 gram | approx. 0.2 gram |
| Pentoxifylline | approx. 1 gram to approx. 20 grams | 8 grams to 12 grams | approx. 10 grams |
| d-alpha tocopheryl acetate | approx. 100 IU to approx. 5000 IU | 250 IU to 500 IU | approx. 350 IU |
| Inactive Ingredient(s) | | | |
| Sodium hyaluronate | 0 to approx. 1 gram | 0.2 mg to 0.4 mg | approx. 0.2 gram |
| Panthenol | 0 to approx. 5 grams | 1 gram to 3 grams | approx. 2 grams |
| Propolis | 0 to approx. 10 grams | 1 gram to 4 grams | approx. 2 grams |
| Sodium metabisulfite | 0 to approx. 1 gram | 0.1 gram to 0.4 gram | approx. 0.2 gram |
| Bifidobacterium longum lysate | 0 to approx. 5 grams | 1 gram to 3 grams | approx. 2 grams |

The composition referenced in Table 2 can be used with the combination of colchicine, pentoxifylline and d-alpha tocopheryl acetate as the active ingredients, along with none or one or more of the inactive ingredients. The active ingredients can be made with none or any of the inactive ingredients.

The surface area depends on the size and location of the cancer. Basically, they have to apply to the whole radiation field (marked by tattoo) as well as outside of the marked field if signs of inflammation (redness, swelling, pain) occur.

TABLE 3 lists the dosage amounts of each of the active ingredients (per 100 ml).

TABLE 3

| Ingredient | Range of dose (per 100 ml) | Narrower range of dose (per 100 ml) | Preferred amount (per 100 ml) | Exact amount (per 100 ml) |
|---|---|---|---|---|
| Colchicine | approx. 0.1 to approx. 1 gram | approx. 0.1 to approx. 0.6 gram | approx. 0.2 to approx. 0.4 gram | approx. 0.2 gram |
| Pentoxifylline | approx. 1 to approx. 20 grams | approx. 5 to approx. 15 grams | approx. 8 to approx. 12 grams | approx. 10 grams |
| Tocopherol | approx. 100 to approx. 5000 IU | approx. 100 to approx. 1000 IU | approx. 250 to approx. 500 IU | approx. 350 IU |

The colchicine dose is based on scientific data (see above −0.2% (0.2 gram per 100 ml) has no side effects and yields same concentration in the dermis 0.5%). Broader doses are in case we need higher concentrations in the future. PTX dose is based on other products that are 10%. Tocopherol dose varies widely in medical and cosmetic products but it gets absorbed well at relatively low concentrations, the dose is based on literature. The dosage can include only colchicine alone with no other active ingredients.

TABLE 4 lists the dosage amounts of each of the inactive ingredients (per 100 ml).

TABLE 4

| Inactive Ingredient(s) | Broad range | Narrow range | Exact amounts |
|---|---|---|---|
| Sodium hyaluronate | 0 to approx. 1 gram | 0.2 mg to 0.4 mg | approx. 0.2 gram |
| Panthenol | 0 to approx. 5 grams | 1 gram to 3 grams | approx. 2 grams |
| Propolis | 0 to approx. 10 grams | 1 gram to 4 grams | approx. 2 grams |
| Sodium metabisulfite | 0 to approx. 1 gram | 0.1 gram to 0.4 gram | approx. 0.2 gram |
| Bifidobacterium longum lysate | 0 to approx. 5 grams | 1 gram to 3 grams | approx. 2 grams |

The inactive ingredients are part of the final cream/gel. It contains everything we mix in when producing the product. We can produce with none, some or all inactives. The benefits of not using inactive ingredients can be used in case someone is allergic to beeswax for example (propolis).

The ability of panthenol to draw moisture into the skin is considered to have a number of benefits, especially because it can significantly penetrate the skin's surface. It plumps the skin, helps reduce the appearance of fine lines and wrinkles, makes skin feel smoother, firmer, and more supple. It is also thought to encourage the generation of new skin cells.

A benefit of using propolis can be its antimicrobial effects and its ability to heal sores and burns. (Gregory S R, Piccolo N, Piccolo M T, Piccolo M S, Heggers J P. "Comparison of propolis skin cream to silver sulfadiazine: a naturopathic alternative to antibiotics in treatment of minor burns." *J Altern Complement Med.* 2002 February; 8 (1):77-83.)

A benefit of using *Bifidobacterium longum* lysate will be described. Reactive skin is characterized by marked sensitivity to physical (heat, cold, wind) or chemical (topically applied products) stimuli and by the impairment of the skin barrier's ability to repair itself. The results of a study demonstrate that this specific bacterial extract has a beneficial effect on reactive skin and can be used for the treatment and/or prevention of symptoms related to reactive skin. (Guéniche A, Bastien P, Ovigne J M, et al. *Bifidobacterium longum* lysate, a new ingredient for reactive skin. *Exp Dermatol.* 2010 August; 19(8): e1-8.)

A benefit of using sodium hyaluronate will now be described. Topically applied sodium hyaluronate can facilitate the absorption of biomacromolecules, i.e. pharmaceuticals, and function like a nanocarrier. (Wickens J M, Alsaab H O, Kesharwani P, et al. Recent advances in hyaluronic acid-decorated nanocarriers for targeted cancer therapy. Drug Discov Today. 2016 Dec. 23. pii: S1359-6446 (16) 30491-3.) It also enhances penetration into the epidermis. (Witting M, Boreham A, Brodwolf R, et al. "Interactions of Hyaluronic Acid with the Skin and Implications for the Dermal Delivery of Biomacromolecules". Mol. Pharmaceutics. 12 (5): 1391-1401. Apr. 14, 2015)

A benefit of using sodium metabisulfite is that it can be used as a disinfectant, antioxidant and preservative agent.

A method of preparing an example of the novel composition will now be described. A Humco Salt Stable Lo base is an improved, stable and durable Pluronic Lecithin Organogel, which is a great delivery system for penetrating the skin and delivering one or many APIs (active pharmaceutical ingredients) through the many layers of skin. The final product can be a cream like dispersion. An example of the composition in USP (United States Pharmacopial convention book of drug information) can include:
Colchicine USP 0.2% (0.2 gram per 100 ml)
Pentoxyfilline USP 10% (10 grams per 100 ml)
Vitamin E D-Alpha Tocophero 100 IU/30 ml (or 350 IU per 100 ml)
Humco Salt Stable LS Advanced Base Qs to final volume All compounding this compound can be performed in an air containment hood. Combining and mixing the APIs and base. The APIs will directly be mixed into the base without a wetting agent, such as propylene glycol, mineral oil, alcohol.

Each API can be weighed out in separate weigh boats which wets the entire surface of the active drug. The weight receipt can be printed out and attached to a batch record.

The calculated Humco base can be weighed plus an additional 10% in the weigh boat. Any excess over the QS (quantity sufficient) can be discarded.

Tare balance with mixing bowl (container vessel) in a tared container, and add 25% of base to bottom of container and coat bottom and sides with a rubber spatula.

Next, add all three APIs into the mixing bowl with base. Gently mix together into the base with a rubber spatula. Next, mix until most large lumps of APIs have been decreased or dissolved.

Next add approximately 50% of base and mix together with a rubber spatula.

QS with the base to the calculated weight on balance.

Hand mixing by mixing with a rubber spatula for 2 minutes by hand.

Initial mixing can include set up mixing vessel into a high speed mixer, and mix at speed 1000 rpms with a mixing time of ten minutes.

For milling set up 3 roller Mill (machine to mix and reduce particle size of compound). Compound will be passed through the mill for approximately three times until particle size is less than 50 microns. The Hegman gauge (measuring tool to measure particle size in a compound) will be used to test compound for correct particle size.

Pass One set back roller at setting 15 and front roller at setting 10.

Pass Two set back roller at setting 12 and front roller at setting 8.

Pass Three set back roller at setting 10 and front roller at setting 6.

Final mixing is to set vessel onto high speed mixer, and mix at speed of 2000 rpms (revolutions per minute), with a mixing time of ten minutes.

Pharmacist Quality Control pH range between 4.5 to 7
Particle size less than 50 microns.
Spread test on ointment slab, and smooth with no streaks or particles.
Odor to be determined after Research and Development and validation.
Specific gravity to be determined after Research and Development and validation.

Warning and Precautions can include keeping the composition out of reach of children, and is to be used for external use only, as directed. Composition should be kept away from light, and needs to be stored at room temperature.

The term "approximately" can be +1-10% of the amount referenced. Additionally, preferred amounts and ranges can include the amounts and ranges referenced without the prefix of being approximately.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A topical colchicine-containing composition, the composition comprising:
   approximately 0.1 weight percent colchicine;
   approximately 1 weight percent to approximately 20 weight percent of pentoxifylline; and
   approximately 100 IU per 100 ml to approximately 5000 IU per 100 ml of d-alpha tocopheryl acetate, wherein the topical composition is applied to the skin for preventing and treating scars due to radiation exposure.

2. The topical colchicine-containing composition of claim 1, wherein the topical composition is in the form of at least one of: suspension, emulsion, solution, gel, paste, ointment, cream, lotion, spray or aerosol.

3. The topical colchicine-containing composition of claim 1, further comprising:
   at least one pharmaceutically acceptable carrier selected from the group consisting of sodium hyaluronate, panthenol, propolis, and sodium metabisulfite.

4. A topical colchicine-containing composition, the composition consisting of:
   an active ingredient for preventing and treating of the formation of scars due to radiation exposure, the active ingredient selected from the group consisting of approximately 0.1 weight percent colchicine, or a combination of approximately 0.1 weight percent colchicine and approximately 1 weight percent to approximately 20 weight percent of pentoxifylline and approximately 100 IU per 100 ml to approximately 5000 IU per 100 ml of d-alpha tocopheryl acetate; and
   at least one pharmaceutically acceptable carrier selected from the group consisting of sodium hyaluronate, panthenol, propolis, and sodium metabisulfite.

5. The topical colchicine-containing composition of claim 4, wherein the active ingredient is the approximately 0.1 weight percent colchicine.

6. The topical colchicine-containing composition of claim 4, wherein the active ingredient is the combination of approximately 0.1 weight percent colchicine and approximately 1 weight percent to approximately 20 weight percent of pentoxifylline and approximately 100 IU per 100 ml to approximately 5000 IU per 100 ml of d-alpha tocopheryl acetate.

* * * * *